United States Patent [19]

Day

[11] Patent Number: 4,945,159

[45] Date of Patent: Jul. 31, 1990

[54] FORMATION OF LACTAMS AND OTHER AMIDES UNDER MILD CONDITIONS BY ACTION OF CYANOGEN

[75] Inventor: Richard A. Day, Cleves, Ohio

[73] Assignee: University of Cincinnati, Cincinnati, Ohio

[21] Appl. No.: 936,891

[22] Filed: Dec. 2, 1986

[51] Int. Cl.$^5$ ............... C07D 501/06; C07D 499/10; C07D 213/127; C07C 102/04

[52] U.S. Cl. ............................ 540/215; 540/217; 540/229; 540/230; 540/316; 546/216; 546/261; 548/450; 564/133; 435/188; 435/45; 435/50

[58] Field of Search ............... 540/316, 314, 215, 217, 540/229, 230; 546/216, 261; 548/450; 564/133

[56] References Cited

U.S. PATENT DOCUMENTS 3,161,634  12/1964  Andersen ............................ 540/316
4,179,557  12/1979  Ishimaru et al. ................ 540/316 X

OTHER PUBLICATIONS

Kirley et al, FEBS Letters, vol. 193, No. 2, pp. 145–149, (Dec. 6, 1985).
Kirley et al, Biochemical and Biophysical Research Communications, vol. 126, No. 1, pp. 457–463, (Jan. 16, 1985).

Primary Examiner—Werren B. Lone
Assistant Examiner—Vera C. Clarke
Attorney, Agent, or Firm—Frost & Jacobs

[57] ABSTRACT

A method for the formation of intramolecular amide bonds by the action of cyanogen, under mild reaction conditions, in the preparation of cyclic amides, including lactams, in biologically active compounds. A compound containing at least one carboxylic acid group and at least one primary or secondary amino group is reacted with cyanogen to form an intramolecular amide bond. The method has utility in the synthesis of B-lactam antibiotics, such as penicillins, cephalosporins, and their derivatives, in enzyme modification, in cyclization of peptides, and in covalent cross-linking of proteins.

10 Claims, No Drawings

FORMATION OF LACTAMS AND OTHER AMIDES UNDER MILD CONDITIONS BY ACTION OF CYANOGEN

FIELD OF THE INVENTION

The present relates generally to a method for the formation of intramolecular amide bonds under mild reaction conditions. More particularly, the invention relates to the use of the method in preparing cyclic amides (including lactams) in biological molecules. Among the compounds to which the method can be applied are penicillins, cephalosporins and other Beta lactams and their derivatives (by B-lactam formation) and intramolecularly cross-linked proteins and enzymes and cyclized peptides.

The present reaction is useful wherever the formation of intramolecular amide bonds under mild reaction conditions is desired.

DISCUSSION OF BACKGROUND AND PRIOR ART

The formation of lactam bonds under mild reaction conditions is important in the synthesis and/or derivitization of many organic compounds. Among these are biologically active compounds which include antibiotics.

Presented below are general instances where lactam bond formation may by found.

I. GENERAL LACTAM FORMATION

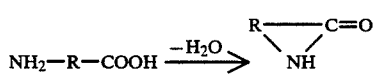

Where R is an organic moiety amenable to cyclization.

II. PEPTIDE BONDING a. Cyclization of Peptides

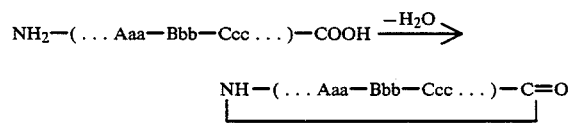

Where (. . . Aaa-Bbb-Ccc. . . ) represents an amino acid sequence.

b. Covalent Crosslinking

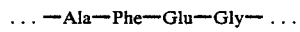 (1)

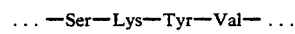 (2)

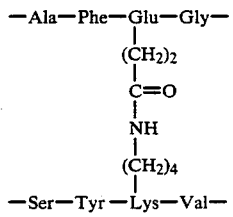

Where amino acid sequences (1) and (2) are contained in the same protein, the cross-linking will be within the same polypeptide chain for proteins that comprise only one polypeptide chain, such as serum albumin or penicillinase. The cross-linking may be within the same polypeptide chain or between polypeptide chains for proteins containing more than one polypeptide chain, such as hemoglobin or chromatin.

III. EZYME MODIFICATION

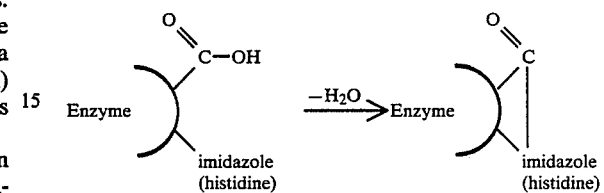

One of the syntheses wherein lactam synthesis is necessary is involved in penicillins and their derivatives. These syntheses include a B-lactam forming step exemplified as follows:

IV. PENICILLIN, CEPHALOSPORIN AND OTHER BETA LACTAM FORMATION

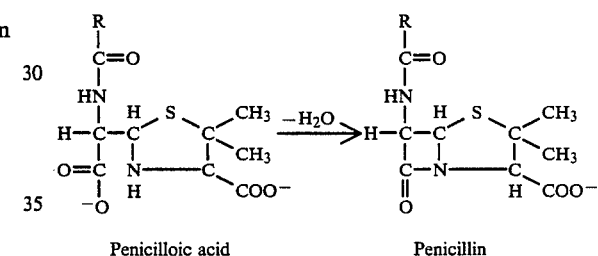

Penicilloic acid      Penicillin

Several methods of synthesizing B-lactams are known in the art. (As used herein, "B-lactams" refer to penicillins and their derivatives, cephalosporins and their derivatives and other B-lactams, unless otherwise indicated).

One such method disclosed by J. C. Sheehan uses treatment of D-α-phenoxymethylpenicilloic acid with N, N¹-dicyclohexyl carbodiimide in dioxane-water at room temperature in the lactam-forming step. Yields of 10-12% of penicillin V potassium (potassium phenoxymethyl penicillinate) were obtained. *The Total Synthesis of Penicillin, Journal Amer. Chem. Soc., Communications to the Editor*, Vol. 79, pp. 1262-1263 (1957).

Another synthesis disloses the conversion of D-α-4-carbomethoxy-5,5-dimethyl-α-trityl-amino-2-thiazolidineacetic acid to 6-tritylamino penicillinate by treatment with N,N'-diisopropyl carbodiimide in dioxane-water. Reported yields of 25% resulted. *A General Synthesis of Penicillins, Journal Amer. Chem. Soc., Communications to the Editor*, Vol. 81, pp. 5838-5850 (1959).

The use of cyanogen and related compounds is known in the synthesis and modification of biological molecules unrelated to amide or lactam formation.

U.S. Pat. No. 3,658,788 (1972) teaches the use of cyanogen with ammonia in solution to form amino oxazolines from reducing sugars. Amino oxazolines form at the hydroxyl group adjacent to the carboxyl or hemiacetal terminus in such sugars in aqueous solution.

U.S. Pat. No. 4,301,282 (1981) relates to the production of bicyclic 1-oxa-B-lactam antibiotics by displacement of the halogen of the corresponding 7-(α-caboxy) acylamino-3-halomethyl-1-oxa-B-lactam with 1-cyanomethyl-1H-tetrazole-5-thiol.

U.S. Pat. No. 4,020,077 (1977) relates to the preparation of 6B-isocyano penicillin and 7B-isocyano cephalosporin esters which are used as intermediates in the synthesis of penicillin and cephalosporin antibiotics. The compound may be prepared by reaction of the corresponding 6B-formamido penicillin ester or 7B-formamido cephalosporin ester with an acid halide derived from phosphorus, sulphur or carbon or from an oxygen acid of one of said elements, suitable halides including thionyl chloride or phosgene, or with a trivalent phosphorus compound such as triphenylphosphine and a halogenated hydrocarbon such as carbon tetrachloride. The conversion of the products to 6B- and 7B-(α-hydroxy) arylacetamido penicillins and cephalosporins respectively by reaction under acidic conditions with an aromatic aldehyde followed by treatment with an aqueous medium is also described.

Other U.S. Patents which described synthesis penicillins and/or cephalosporin and their derivatives include U.S. Pat. Nos. 3,994,883 (1976); 3,989,685 (1976); 4,020,077 (1977); 4,051,132 (1977); 4,072,677 (1978); 4,167,630 (1979); 4,248,966 (1981); 4,251,442 (1981); 4,307,192 (1981); 4,320,055 (1982); 4,452,796 (1984); and 4,536,393 (1985).

All of the references discussed and/or mentioned above are hereby incorporated by reference. Also incorporated herein by reference is the article: *Cyanogen-indiced B-glutamyl to imidazole cross-link in carbonic anhydrase, F.E.B.S. Letters*, 3180, volume 193, number 2, pp. 145-149 (1985).

It is desirable to be able to form lactams under mild conditions because it saves energy and generally can result in higher yields due to less reactant, intermediate or product breakdown.

In addition, when these syntheses are performed at or near physiologic conditions, it generally allows more realistic, reliable and feasible research. This is especially true in enzyme studies where active sites are studied by their modification to measure binding affinity changes. It is desirable to be able to modify enzymes at or near physiologic conditions with as few intermediates as possible to increase yield of the modified enzyme. It is further generally better to utilize modification reactions which yield few by-products which can adversely affect binding affinity studies.

Also important is to have a modifying reaction in which no additional molecular moieties become incorporated into the enzyme. Such a reaction allows one to better correlate binding afinity to active site residues to assess their importance in enzyme activity. Reactions of this type include cyclization reactions, such as B-lactam formation which modify active sites without adding additional molecular moieties.

An important advantage of the use of mild reaction conditions is that it favors intramolecular reactions over intermolecular reactions. A second important property is that the formation of relatively strained, i.e. four- or seven-numbered ring systems, and relatively non-strained, i.e. five- or six-numbered ring systems, occurs at comparable rates and yields. For instance, where the reactants contain more than one reactive group, or where the desired reaction in intramolecular (i.e. where both intramolecular and intermolecular amide formation is possible), the synthesis can be done without undesirable side reactions (i.e. intermolecular bonding where intramolecular bonding is sought).

It is additionally advantageous to be able to perform selective intramolecular reactions which minimize the need for functional group blocking. Minimizing blocking generally results in higher overall yields.

All of the abovce purposes are furthered by the present inventive method which provides a method of producing amides, particularly lactams, under mild conditions.

SUMMARY OF THE INVENTION

The present invention relates to the formation of an intramolecular amide bond in a reactant containing at least one carboxylic acid group and at least one primary or secondary amine group. The invention further relates to lactam formation by reacting a single compound containing both at least one carboxylic group and at least one primary or secondary amine group. In lactam-forming reactions and reactions involving both polypeptides or proteins, the reactants are treated with cyanogen (oxalic acid dinitrile; $C_2N_2$) for sufficient time and at sufficient temperature to allow the desired lactam compound to form.

The reactions of the present invention are generally carried out at lower temperatures although higher temperatures (i.e. $>25°$ C.) can be used. The process can be done at atmopsheric pressure or at pressure above 1 atmosphere.

DETAILED DESCRIPTION OF THE PREFERRED EMBODIMENTS

The reaction of the present invention can be performed on any given organic compound provided that it contain at lest one carboxylic acid moiety and at least one primary or secondary amine group. Of course, the reactant must have as a threshold property a molecular geometry which makes them amenable to cyclization. That is, they must have a molecular arrangement which allows the formation of a cycle of any given number of atoms upon formation of the cyclic amide bond. Also, in cyclization reactions, the preferred reactants are those which will give stable cyclic geometries once the lactam is formed.

With regard to the use of the inventive method in forming pencillins, cephalosporins or other B-lactams and their derivatives by lactam ring closure, the inventive reaction can be applied to any such derivative or precursor thereof which is amenable to lactam ring closure at the appropriate point in a total synthesis. For example, this is normally done in forming the B-lactam-thiazolidine ring system in penicillins. Because lactam ring formation may be at various stages in a total synthesis, the precursor or derivative which requires at least a lactam ring to form a penicillin, cephalosporin or other B-lactams shall be referred to herein as "lactam-requiring" precursors of pencillins, cephalosporins or other B-latams. For the purposes of this application, all non-enzyme applications of the inventive method are referred to collectively as "industrial" applications.

In the application of the inventive method to enzyme modification, it is possible to use any enzyme which contains at least one carboxylic acid an one primary or secondary amine group, preferably in the proper spatial relationship to accommodate lactam geometry when the enzyme is in its active form. It is, of course, preferred that the enzyme have an acid and amine group on residues which are in some way related to the enzymes activity, such as in its active site.

Examples of enzymes which can be modified using the inventive method may include oxidoreductases, hydrolases, isomerases, ligases, transferases, and lyases.

With regard to temperature, industrial applications of the inventive method will generally be performed at temperatures above 0° C. The upper temperature limit in such an application is controlled by the breakdown of products or reactants which will normally be determined on a case-by-case basis. However, the preferred temperature will be within the range of from about 0° to about 100° C.; an even more preferred range is from about 0° C. to about 25° C.

Because of the criticality of temperature to the preservation of enzyme structure, enzyme modification using the inventive method is preferably carried out at lower temperatures. A general temperature range for these types of reactions is in the range of from about 0° C. to 25° C. The preferred temperature for enzyme modification is 0° C. Cooling can be done by conventional means, such as ice baths, liquified gas, frozen liquid slushes, or mechanical cooling devices.

Cyanogen (oxalic acid dinitrile N C C N) is a gas with a boiling point of about −21.2° C. At reaction temperatures above the boiling point of cyanogen, it has been found that increased yields can result from higher partial pressures of cyanogen in the reaction mixture. The partial pressure of the cyanogen used in the reaction mixture will normally be dictated by the desired stoichiometry between the cyanogen and the reactants. In higher volume industrial applications, the amount of cyanogen used will normally be adjusted as nearly to stoichiometric amounts as possible to avoid the harmful effects of excess cyanogen and its by-products (i.e. cyanide gas).

The solvent used in the method of the invention can generally be described as "semiaqueous". As used herein "semiaqueous" is intended to mean solutions which are in some part water with the balance being a water-misible organic liquid. Examples of the organic liquid which can be used in the present invention include acetonitrile, dimethyl formamide, dioxane, tetrahydrofuran, DIGLYME ® (dimethyl ether of glycol), dimethylsulfoxide (DMSO), pyridine, and water-miscible ethers. Alcohols are preferably not used as a solvent component in the synthesis of penicillins or cephalosporins.

The ratio of water to the organic liquid in these "semiaqueous" solvents are preferably adjusted to maximum organic liquid content. This is often limited by the solubility of the reactants. For instance, the solvent used for synthesis of penicillins and cephalosporins is in the range of from about 50% to about 90% aqueous. Other reactants can tolerate lower water content. Semiaqueous solvents can also be used in practicing the inventive method to cyclize peptides.

In enzyme modification applications, the preferred solvent is pure water due to the generally adverse denaturing effect of organic solvents on enzymes.

The pH of the reactant solution should be adjusted to a value below 6.5; preferably pH 5 or below. This can be done with a mineral acid, preferably hydrochloric acid. Above pH 6.5 yields are greatly reduced. This is thought to be due to the decomposition of the cyanogen under basic conditions. In some instances, the pH will be lowered upon the solution contacting the cyanogen gas.

The concentration of the reactant will depend on the particular application of the inventive method and of course will be limited by reactant solubility. Reactant concentration will generally range from about 0.001 to about 0.1M, with the preferred range being in the range of from about 0.05 to about 0.1M.

In enzyme modification applications, the concentration of enzyme will generally be below 10 mg/ml, preferably in the range of from about 1 to about 10 mg/ml. Higher concentrations can be used.

When more than one reactive group per reactant is involved, a synthetic strategy can be built around minimal functional group blocking. Functional group blocking generally decreases yields by addition steps to a total synthesis. This feature is particularly important to B-lactam formation in pencillins, cephalosporins and related antibiotics.

The following examples are illustrative of the preferred embodiments of the invention in its applications. Variation of process parameters will be obvious to one skilled in the art in light of the following examples.

EXAMPE I—BETA LACTAM FORMATION IN PENICILLIN

A solution of 6-amino penicilloic acid having a concentration of about 2.15 mg/ml (about 0.01 molar) is prepared in 90% dimethylformamide in water. The solution is adjusted to a pH of 5 with 6 N HCl. 1 ml of the solution is placed in a sealable 100×13 mm test tube. After chilling the solution in an ice bath, 10 cc of cyanogen ($C_2N_2$) is added to the head space. The reaction is then stirred for sufficient time to allow the lactam product to form. The formation of the penicillin in the reaction can be verified and monitored by thin layer chromatography, nuclear magnetic resonance and/or by assay with *Bacillus subtilis*. The results showed the cyclization of the precursor penicilloic acid to be essentially quantitative.

EXAMPLE II—BETA LACTAM FORMATION IN PENICILLIN

The same procedure is followed as in Example I, with the exception that the pH is not adjusted with hydrochloric acid. Rather, the pH moves from an initial value of approximately pH 8 to a value of approximately pH 6 after contacting the cyanogen gas. The results were verified and monitored as in Example I and likewise showed quantitative conversion of the precursor penicilloic acid.

EXAMPLE III—BETA-LACTAM FORMATION IN PENICILLIN G

The same procedure is followed as in Examples I and II, with the exception that the reactant is the Beta-Lactam-requiring precursor of penicillin G (i.e. benzyl penicilloic acid). The amount of precursor conversion was in the range of from about 40 to about 50%.

EXAMPLE IV—BETA-LACTAM FORMATION IN PENICILLIN V

The same procedure is followed as in Example I or II wherein the reactant is the Beta-Lactam-requiring precursor of penicillin V (plenoxymethyl penicilloic acid). The amount of precursor conversion was in the range of from about 40 to about 50%.

EXAMPLE V—ENZYME MODIFICATION

An aqueous solution of carbonic anhydrase from bovine erythrocytes was prepared in a concentration of $5\times10^{-5}$M and placed in a sealable glass container. An aliquot of cyanogen gas equivalent to a concentration of $5\times10^{-3}$M was injected into the head space. The reaction mixture was incubated for a period of about two hours at room temperature. The reaction was monitored by change in enzymatic activity. The results showed essentially stoichiometric conversion of the enzyme to its modified form as determined by amino acid analysis.

What is claimed is:

1. A method of preparing a cyclic amide comprising reacting (1) an organic compound containing at least one carboxylic acid group and at least one group selected from the group consisting of primary and secondary amino groups with (2) cyanogen for sufficient time and at sufficient temperature and pressure to form at least one intramolecular amide bond within said organic compound.

2. The method of claim 1 wherein the temperature of said reaction is in the range of from about 0° C. to about 100° C.

3. The method of claim 1 wherein the temperature of said reaction is in the range of from about 0° C. to about 25° C.

4. The method of claim 1 wherein the total atmospheric pressure maintained above said reaction is about 1 atm. or above.

5. The method of claim 2 wherein the pH of said reaction is below 6.5.

6. The method of claim 1 wherein said organic compound is selected from the group consisting of lactam-requirim precursors of penicillins, cephalosporins, and other beta-lactams.

7. The method of claim 1 wherein a solvent is used in said reaction, and said solvent is a semiaqueous solvent having an aqueous portion and a non-aqueous portion.

8. The method of claim 7 wherein the solvent is free of alcohol.

9. The method of claim 7 wherein the non-aqueous portion of said semiaqueous solvent is selected from the group consisting of diemthylformamide, dimethylsulfoxide, tetrahydrofuran, pyridine, DIGLYME®, and water-miscible ethers.

10. A method of preparing a cyclic amide comprising recting (1) a compound selected from the group consisting of lactam-requiring precursors of penicillins, cephalosporins and other beta-lactams containing at least one carboxylic acid group and at least one group selected from the group consisting of primary and secondary amino groups with (2) cyanogen for sufficient time and at sufficient temperature and pressure to form at least one intramolecular amide bond within said organic compound.

* * * * *